United States Patent
Jungkamp et al.

(10) Patent No.: US 6,852,199 B2
(45) Date of Patent: Feb. 8, 2005

(54) METHOD FOR SEPARATING PENTENENITRILE ISOMERS

(75) Inventors: Tim Jungkamp, Dossenhein (DE); Dagmar Pascale Kunsmann-Keitel, Limburgerhof (DE); Robert Baumann, Mannheim (DE); Peter Bassler, Viernheim (DE); Wolfgang Siegel, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 132 days.

(21) Appl. No.: 10/381,338

(22) PCT Filed: Sep. 25, 2001

(86) PCT No.: PCT/EP01/11050
§ 371 (c)(1),
(2), (4) Date: Mar. 25, 2003

(87) PCT Pub. No.: WO02/26698
PCT Pub. Date: Apr. 4, 2002

(65) Prior Publication Data
US 2004/0039221 A1 Feb. 26, 2004

(30) Foreign Application Priority Data
Sep. 28, 2000 (DE) .......................................... 100 49 265

(51) Int. Cl.$^7$ ............................. B01D 3/36; B01D 3/38; C07C 253/34; C07C 255/07
(52) U.S. Cl. ............................. 203/91; 203/92; 203/93; 203/94; 203/95; 203/96; 203/97; 203/98; 558/463
(58) Field of Search ................................. 203/91–98, 1, 203/2, 14, 100; 558/355, 463, 465

(56) References Cited

U.S. PATENT DOCUMENTS

| 2,666,748 A | * | 1/1954 | Arthur, Jr. et al. .......... 502/175 |
| 3,526,654 A | | 9/1970 | Hildebrand |
| 3,564,040 A | | 2/1971 | Downing et al. |
| 3,852,325 A | | 12/1974 | King |
| 3,852,327 A | | 12/1974 | Durliner et al. |
| 3,865,865 A | | 2/1975 | Musser et al. |
| 5,002,639 A | * | 3/1991 | Steck et al. .................... 203/48 |
| 6,242,633 B1 | | 6/2001 | Fischer et al. |

OTHER PUBLICATIONS

Weissermel, J.Arpe, Ind.Org.Chem.,4.Aufl, 266ff.
Applied Homogeneous Catalysis . . . vol. 1,465–486–Huthmacher et al.
Kirk–Othmer, Enc.chem.tech.3.Ed.vol. 7,1979,870–881.
Ullmann's Enc.Ind.Chem.vol. B3,5Ed,1988,Seite 6–14 bis 6–22.

* cited by examiner

Primary Examiner—Virginia Manoharan
(74) Attorney, Agent, or Firm—Keil & Weinkauf

(57) ABSTRACT

A process is provided for the distillative separation of pentene nitrile isomers which have a relative volatility alpha ranging from 1.0 to 1.3 in the pressure range from 1 to 500 kPa, wherein the distillation is carried out in the presence of a liquid diluent which forms with the pentene nitrile isomers, under the same pressure conditions, azeotropes whose relative volatility alpha is higher than that of the pentene nitrile isomers to be separated.

10 Claims, No Drawings

METHOD FOR SEPARATING PENTENENITRILE ISOMERS

The present invention relates to a process for the distillative separation of pentene nitrile isomers which have a relative volatility alpha ranging from 1.0 to 1.3 in the pressure range from 1 to 500 kPa, wherein the distillation is carried out in the presence of a liquid diluent which forms with the pentene nitrile isomers, under the same pressure conditions, azeotropes whose relative volatility alpha is higher than that of the pentene nitrile isomers to be separated.

The industrial production of polyamides has created a large global demand for alpha,omega-alkylenediamines, which are used as an important raw material. Alpha,omega-alkylenediamines, e.g. hexamethylenediamine, are almost exclusively obtained by hydrogenation of the corresponding dinitriles. Virtually all the industrial methods of producing hexamethylenediamine are therefore essentially variants of adipodinitrile production, which globally amounts to about 1.0 million tonnes per annum.

K. Weissermel, H. -J. Arpe, Industrielle Organische Chemie (Industrial Organic Chemistry), 4th edition, VCH Weinheim, p. 266 et seq., describes four fundamentally different routes for the production of adipodinitrile:

1. the dehydrating amination of adipic acid with ammonia in the liquid or gas phase via intermediate diamide;
2. the indirect hydrocyanation of 1,3-butadiene via intermediate 1,4-dichlorobutenes;
3. the hydrodimerization of acrylonitrile in an electrochemical process; and
4. the direct hydrocyanation of 1,3-butadiene with hydrogen cyanide.

In a first stage, the last of these processes yields, by monoaddition, a mixture of isomeric pentene nitriles such as trans-2-pentene nitrile, cis-2-pentene nitrile, trans-3-pentene nitrile, cis-3-pentene nitrile, 4-pentene nitrile, (E)-2-methyl-2-butene nitrile, (Z)-2-methyl-2-butene nitrile and 2-methyl-3-butene nitrile.

In a subsequent stage, adipodinitrile is then formed by an anti-Markownikow hydrogen cyanide addition onto 4-pentene nitrile. The reaction takes place in the liquid phase in a solvent, e.g. tetrahydrofuran, at a temperature ranging from 30 to 150° C. and under atmospheric pressure. Nickel complexes with phosphorus-containing ligands are used as catalysts and Lewis acids, such as metal salts or triphenylboron, are optionally used as promoters. In this second hydrogen cyanide addition, other pentene nitrile isomers are also formed from 4-pentene nitrile or the isomers in equilibrium therewith, such as trans-3-pentene nitrile, cis-3-pentene nitrile and 2-methyl-3-butene nitrile or mixtures thereof.

"Applied Homogeneous Catalysis with Organometalic [sic] Compounds", Vol. 1, VCH Weinheim, p. 465 et seq., describes in general terms the heterogeneously and homogeneously catalyzed addition of hydrogen cyanide onto olefins, the principal catalysts used being based on phosphine, phosphite and phosphinite complexes of nickel and palladium. The preparation of adipodinitrile by the hydrocyanation of butadiene uses predominantly nickel(0) phosphite catalysts, optionally in the presence of a Lewis acid as promoter. The formation of the monoaddition product yields an isomer mixture comprising, inter alia, 3-pentene nitrile and 2-methyl-3-butene nitrile.

WO 99/13983 describes the hydrocyanation of butadiene or a hydrocarbon mixture containing 1,3-butadiene to give monoolefinic $C_5$ mononitriles and/or adipodinitrile in the presence of nickel phosphonite complexes. Mixtures of pentene nitrile isomers are again obtained here.

Before the second hydrogen cyanide addition, it is desirable to separate off those pentene nitrile isomers which cannot easily be converted to adipodinitrile or which form by-products. It is also desirable to separate the mixture of pentene nitrile isomers which is obtained as a by-product in the adipodinitrile synthesis.

The distillative separation of this isomer mixture creates considerable problems because the relative volatility alpha of certain pentene nitrile isomers ranges from 1.0 to 1.3 in the 1 to 500 kPa range. The relative volatility alpha is understood as meaning the ratio of the vapor pressures of two substances, the vapor pressure of the substance with the higher vapor pressure forming the numerator of the ratio.

Particularly suitable mixtures for this purpose are those which contain the pentene nitrile combinations trans-3-pentene nitrile/4-pentene nitrile, trans-3-pentene nitrile/trans-2-pentene nitrile, trans-2-pentene nitrile/4-pentene nitrile, cis-3-pentene nitrile/4-pentene nitrile, cis-3-pentene nitrile/trans-2-pentene nitrile or (E)-2-methyl-2-butene nitrile/2-methyl-3-butene nitrile.

To circumvent the problem of separating trans-3-pentene nitrile and trans-2-pentene nitrile, it was proposed, e.g. in U.S. Pat. No. 3,526,654, U.S. Pat. No. 3,564,040, U.S. Pat. No. 3,852,325 and U.S. Pat. No. 3,852,327, catalytically to convert the pentene nitrile isomers which cannot easily be separated off by distillation into ones which can easily be separated off by distillation.

The disadvantage here is that the catalytic isomerization results in losses of valuable product due to the formation of unwanted isomers or oligomers.

It is an object of the present invention to provide a process which affords, in a technically simple and economical manner, the distillative separation of pentene nitrile isomers which have a relative volatility alpha ranging from 1.0 to 1.3 in the pressure range from 1 to 500 kPa.

We have found that this object is achieved by the process defined at the outset.

The process according to the invention can advantageously be applied to the separation of pentene nitrile isomers which have a relative volatility alpha ranging from 1.0 to 1.3, preferably from 1.0 to 1.2 and particularly preferably from 1.0 to 1.15, in the pressure range from 1 to 500 kPa. Particularly suitable mixtures are those which contain the abovementioned combinations of pentene nitrile isomers.

In one preferred embodiment of the process, a mixture containing trans-3-pentene nitrile and trans-2-pentene nitrile yields a mixture in which the ratio of trans-2-pentene nitrile to trans-3-pentene nitrile is higher than in the starting mixture, and a mixture in which the ratio of trans-2-pentene nitrile to trans-3-pentene nitrile is lower than in the starting mixture.

In another preferred embodiment of the process, a mixture containing trans-3-pentene nitrile and 4-pentene nitrile yields a mixture in which the ratio of trans-3-pentene nitrile to 4-pentene nitrile is higher than in the starting mixture, and a mixture in which the ratio of trans-3-pentene nitrile to 4-pentene nitrile is lower than in the starting mixture.

In another preferred embodiment of the process, a mixture containing trans-2-pentene nitrile and 4-pentene nitrile yields a mixture in which the ratio of trans-2-pentene nitrile to 4-pentene nitrile is higher than in the starting mixture, and a mixture in which the ratio of trans-2-pentene nitrile to 4-pentene nitrile is lower than in the starting mixture.

In another preferred embodiment of the process, a mixture containing cis-3-pentene nitrile and 4-pentene nitrile yields a mixture in which the ratio of cis-3-pentene nitrile to 4-pentene nitrile is higher than in the starting mixture, and a mixture in which the ratio of cis-3-pentene nitrile to 4-pentene nitrile is lower than in the starting mixture.

In another preferred embodiment of the process, a mixture containing cis-3-pentene nitrile and trans-2-pentene nitrile yields a mixture in which the ratio of cis-3-pentene nitrile to trans-2-pentene nitrile is higher than in the starting mixture, and a mixture in which the ratio of cis-3-pentene nitrile to trans-2-pentene nitrile is lower than in the starting mixture.

In another preferred embodiment of the process, a mixture containing (E)-2-methyl-2-butene nitrile and 2-methyl-3-butene nitrile yields a mixture in which the ratio of (E)-2-methyl-2-butene nitrile to 2-methyl-3-butene nitrile is higher than in the starting mixture, and a mixture in which the ratio of (E)-2-methyl-2-butene nitrile to 2-methyl-3-butene nitrile is lower than in the starting mixture.

The preparation of the mixture of pentene nitrile isomers used in the process according to the invention, especially by the addition of hydrogen cyanide onto butadiene or hydrocarbon mixtures containing butadiene, can be carried out by processes known per se, especially by the addition of hydrogen cyanide onto butadiene or hydrocarbon mixtures containing butadiene, for example as described at the outset. In principle, according to previous observations, the application of the process according to the invention in neither restricted nor excluded by the type of preparation of the pentene nitrile isomers or by the quantitative composition of the isomer mixture.

According to the invention, the distillation is led [sic] carried out in the presence of a liquid diluent which forms with the pentene nitrile isomers, under the same pressure conditions, azeotropes whose relative volatility alpha is higher, preferable at least 1% higher, than that of the pentene nitrile isomers to be separated.

The amount of liquid diluent compared with the amount of mixture of pentene nitrile isomers is not critical per se. If the amount of liquid diluent used is greater than that which corresponds to the amounts to be distilled off via the azeotropes, excess liquid diluent remains as bottom product. If the amount of liquid diluent used is less than that which corresponds to the amounts to be distilled off via the azeotropes, excess mixture of pentene nitrile isomers remains as bottom product. It has proved advantageous to use an amount of liquid diluent, compared with the amount of mixture of pentene nitrile isomers, which corresponds to the amounts to be distilled off via the azeotropes.

The distillation can advantageously be carried out at a pressure ranging from 1 to 200 kPa, preferably from 50 to 100 kPa, and especially under atmospheric pressure.

The distillation can advantageously be carried out as a fractional distillation in one or more, such as 2 or 3, distillation apparatuses.

Suitable apparatuses are those conventionally used for distillation, for example the ones described in Kirk-Othmer, Encyclopedia of Chemical Technology, 3rd Ed., Vol. 7, John Wiley & Sons, New York, 1979, pages 870–881, such as sieve-plate columns, bubble-cap columns, packed columns, columns with a side discharge or columns with dividing walls.

In one preferred embodiment, the liquid diluent used exhibits a miscibility gap with pentene nitrile isomers under specific quantity conditions, pressure conditions (preferably ranging from 10 to 200 kPa and especially atmospheric pressure) and temperature conditions (preferably ranging from 0 to 120° C. and especially ambient temperature).

Preferably, the product mixture can be separated into two phases by the choice of a suitable temperature. A further possibility is the choice of suitable proportions, such as the addition of liquid diluent.

The phase separation can be effected in a manner known per se in apparatuses described for such purposes, for example those known from Ullmann's Encyclopedia of Industrial Chemistry, Vol. B3, 5th Ed., VCH Verlagsgesellschaft, Weinheim, 1988, pages 6–14 to 6–22.

The optimum apparatuses and process conditions for the phase separation can easily be determined by means of a few simple preliminary experiments.

Advantageously, all or part of that phase of the two which contains the higher proportion by weight of liquid diluent after the phase separation can be recycled into the process according to the invention.

Suitable liquid diluents are organic or inorganic liquid diluents. In one advantageous embodiment, it is possible to used [sic] water as the liquid diluent.

The pentene nitrile isomers obtained in the process according to the invention which can be fed into another economical hydrogen cyanide addition can then be converted to adipodinitrile in a manner known per se.

The pentene nitrile isomers obtained in the process according to the invention which cannot be fed into another economical hydrogen cyanide addition can then be isomerized to other pentene nitrile isomers in a manner known per se.

EXAMPLES

EXAMPLES ACCORDING TO THE INVENTION

A mixture of 800 g of a mixture of pentene nitrile isomers according to table 1 and 800 g of water was fractionally distilled under atmospheric pressure in a distillation column (height: 185 cm, diameter: 30 mm, packing: Sulzerpack EX, Sulzer Chemtec AG, Winterthur, Switzerland) with a reflux ratio of 1:5 (discharge:reflux). The samples obtained as the top fraction were analyzed by gas chromatography.

COMPARATIVE EXAMPLES

The comparative examples were carried out in the same way as the examples according to the invention except that 1600 g of mixture of pentene nitrile isomers according to table 1 were used without any water.

TABLE 1

| | Combination of pentene nitrile isomers | Ratio of GC areas | | Distill. temp. |
|---|---|---|---|---|
| | | Before distill. | After distill. | |
| Ex. 1 | trans-2-pentene nitrile/trans-3-pentene nitrile | 1.9 | 3.4 | 92° C. |
| Comp. Ex. 1 | trans-2-pentene nitrile/trans-3-pentene nitrile | 2.2 | 1.6 | 142° C. |
| Ex. 2 | trans-3-pentene nitrile/4-pentene nitrile | 4.5 | 26 | 94° C. |
| Comp. Ex. 2 | trans-3-pentene nitrile/4-pentene nitrile | 4.4 | 7.1 | 132° C. |
| Ex. 3 | (E)-2-methyl-2-butene nitrile/2-methyl-3-butene nitrile | 6.0 | 20 | 87° C. |
| Comp. Ex. 3 | (E)-2-methyl-2-butene nitrile/2-methyl-3-butene nitrile | 6.0 | 14 | 117° C. |

What is claimed is:

1. A process for the distillative separation of pentene nitrile isomers which have a relative volatility alpha ranging from 1.0 to 1.3 in the pressure range from 1 to 500 kPa, wherein the distillation is carried out in the presence of a liquid diluent which forms with the pentene nitrile isomers, under the same pressure conditions, azeotropes whose relative volatility alpha is higher than that of the pentene nitrile isomers to be separated.

2. A process as claimed in claim 1 wherein the liquid diluent exhibits a miscibility gap with pentene nitrile isomers under specific quantity, pressure and temperature conditions.

3. A process as claimed in claim 2 wherein a mixture obtained in the distillation is separated into two phases and that phase of the two which contains the higher proportion by weight of liquid diluent is recycled into the process as claimed in claim 1.

4. A process as claimed in claim 1 wherein the liquid diluent used is water.

5. A process as claimed in claim 1 wherein a mixture containing trans-3-pentene nitrile and trans-2-pentene nitrile yields a mixture in which the ratio of trans-2-pentene nitrile to trans-3-pentene nitrile is higher than in the starting mixture, and a mixture in which the ratio of trans-2-pentene nitrile to trans-3-pentene nitrile is lower than in the starting mixture.

6. A process as claimed in claim 1 wherein a mixture containing trans-3-pentene nitrile and 4-pentene nitrile yields a mixture in which the ratio of trans-3-pentene nitrile to 4-pentene nitrile is higher than in the starting mixture, and a mixture in which the ratio of trans-3-pentene nitrile to 4-pentene nitrile is lower than in the starting mixture.

7. A process as claimed in claim 1 wherein a mixture containing trans-2-pentene nicrile and 4-pentene nitrile yields a mixture in which the ratio of trans-2-pentene nitrile to 4-pentene nitrile is higher than in the starting mixture, and a mixture in which the ratio of trans-2-pentene nitrile to 4-pentene nitrile is lower than in the starting mixture.

8. A process as claimed in claim 1 wherein a mixture containing cis-3-pentene nitrile and 4-pentene nitrile yields a mixture in which the ratio of cis-3-pentene nitrile to 4-pentene nitrile is higher than in the starting mixture, and a mixture in which the ratio of cis-3-pentene nitrile to 4-pentene nitrile is lower than in the starting mixture.

9. A process as claimed in claim 1 wherein a Mixture containing cis-3-pentene nitrile and trans-2-pentene nitrile yields a mixture in which the ratio of cis-3-pentene nitrile to trans-2-pentene nitrile is higher than in the starting mixture, and a mixture in which the ratio of cis-3-pentene nitrile to trans-2-pentene nitrile is lower than in the starting mixture.

10. A process as claimed in claim 1 wherein a mixture containing (E)-2-methyl-2-butene nitrile and 2-methyl-3-butene nitrile yields a mixture in which the ratio of (E)-2-methyl-2-butene nitrile to 2-methyl-3-butene nitrile is higher than in the starting mixture, and a mixture in which the ratio of (E)-2-methyl-2-butene nitrile to 2-methyl-3-butene nitrile is lower than in the starting mixture.

* * * * *

UNITED STATES PATENT AND TRADEMARK OFFICE
CERTIFICATE OF CORRECTION

PATENT NO. : 6,852,199 B2
DATED : February 8, 2005
INVENTOR(S) : Jungkamp et al.

It is certified that error appears in the above-identified patent and that said Letters Patent is hereby corrected as shown below:

Column 6,
Line 22, "nicrile" should read -- nitrile --.
Line 33, "Mixture" should read -- mixture --.

Signed and Sealed this

Sixth Day of June, 2006

JON W. DUDAS
*Director of the United States Patent and Trademark Office*